United States Patent
Wormser et al.

(10) Patent No.: US 6,926,913 B2
(45) Date of Patent: Aug. 9, 2005

(54) COMPOSITION CONTAINING MOLECULAR IODINE

(75) Inventors: Uri Wormser, Jerusalem (IL); Amnon Sintov, Omer (IL)

(73) Assignees: Ben Gurion University of the Negev Research & Development Authority, Beersheva (IL); Yissum Research Development Company of the Hebrew, Jerusalem (IL)

( * ) Notice: Subject to any disclaimer, the term of this patent is extended or adjusted under 35 U.S.C. 154(b) by 55 days.

(21) Appl. No.: 10/257,360

(22) PCT Filed: Mar. 22, 2001

(86) PCT No.: PCT/IL01/00277

§ 371 (c)(1),
(2), (4) Date: Nov. 19, 2002

(87) PCT Pub. No.: WO01/70242

PCT Pub. Date: Sep. 27, 2001

(65) Prior Publication Data

US 2004/0081707 A1 Apr. 29, 2004

(30) Foreign Application Priority Data

Mar. 22, 2000 (IL) .................................. 135222

(51) Int. Cl.$^7$ .................. A61K 33/18; A61K 31/34; A61K 31/357; A61K 31/045; A61P 17/02

(52) U.S. Cl. .................. 424/667; 424/668; 424/669; 424/670; 424/671; 424/672; 424/DIG. 13; 514/461; 514/467; 514/724; 514/738; 514/887; 514/970; 514/971

(58) Field of Search .................. 424/667–672, 424/DIG. 13; 514/461, 467, 724, 738, 887, 970, 971

(56) References Cited

U.S. PATENT DOCUMENTS 6,667,052 B2 * 12/2003 Sintov et al. ............... 424/449

FOREIGN PATENT DOCUMENTS

EP 0 649 660 A 4/1995

OTHER PUBLICATIONS

Martindale The Extra Pharmacopoeia, The Pharmaceutical Press, London, 1993, p. 972.*

* cited by examiner

*Primary Examiner*—John Pak
(74) *Attorney, Agent, or Firm*—Foley & Lardner LLP

(57) ABSTRACT

The invention provides a composition of matter comprising molecular iodine and tetraglycol.

13 Claims, 15 Drawing Sheets

Effect of vehicle on SM skin toxicity

Protective effect of iodine against SM vapor

Effect of iodine on thermal burns

*E. coli*
2% Iodine New Formulation

*Bacillus subtilis*
2% Iodine New Formulation

*Ps. putida*
2% Iodine New Formulation

*E, coli*
2% Iodine New Formulation

*Bacillus subtilis*
2% Iodine New Formulation

*Ps. putida*
2% Iodine New Formulation

E.coli
2% Iodine Tincture

Bacillus subtilis
2% Iodine Tincture

*Ps. putida*
2% Iodine Tincture

*E. coli*
2% Iodine Solution

Bacillus subtilis
2% Iodine Solution

Ps. putida
2% Iodine Solution

*E. coli*
10% Povidone-Iodine New Formulation

*Bacillus subtilis*
10% Povidone-Iodine New Formulation

Ps. putida
10% Povidone-Iodine New Formulation

E coli
10% Povidine-Iodine (polydine) Sol.

*Bacillus subtilis*
10% Povidine-Iodine (polydine) Sol.

*Ps. putida*
10% Povidine-Iodine (polydine) Sol.

COMPOSITION CONTAINING MOLECULAR IODINE

The present invention relates to a new iodine formulation composed of tetraglycol (glycofurol, tetrahydrofurfuryl alcohol polyethyleneglycol ether) (TG) as a solvent of molecular iodine ($I_2$). The uniqueness of the formulation is that molecular iodine solution in TG remains stable even in the presence of water in the preparation, in contrast to other iodine solvents, such as ethanol in which iodine precipitates after water addition.

This preparation possesses potent antiseptic properties as compared to the currently available iodine preparations. In addition, the offered formulation possesses potent counter-irritating properties. Previous studies have shown that post-exposure treatment with povidone iodine protects the skin against chemical and thermal stimuli. It was demonstrated that topical treatment with povidone-iodine 10 min after sulfur mustard exposure significantly protected the skin against the irritant, while longer interval of 20 min was also effective but to a lesser extent. However, the present iodine formulation was still effective at interval of 30 min (and 45 min to a lesser extent) between exposure and treatment. Thermal burns are also beneficially affected by the present iodine preparation. Exposure of skin to hot water followed by topical treatment with iodine reduced tissue damage as compared to the non-treated area.

Iodine and iodine complex preparations are widely employed as disinfectants in human and veterinary medicine. Iodine has a powerful bactericidal and fungicidal action and is also active against viruses. They are used as topical antiseptic agents for treatment of small wounds, abrasions and other skin lesions such as herpes simplex. They are used for preoperative treatment of the skin area to be dissected. Iodine preparations are also used in veterinary medicine as post-milking disinfecting treatment of the udders. Iodine is also effectively used for drinking water and swimming pool water disinfection (Martindale, The extra pharmacopoeia, 28th edition, Eds.: Reynolds, J. E. F. and Prasad, A. B., The Pharmaceutical Press, London, 1982, pp. 862–864).

Topical iodine preparations possess counter-irritating activity in rheumatism, tenosynovitis and in inflammatory diseases of the peripheral nervous system and muscles (Martindale, The extra pharmacopoeia, 28th edition, Eds.: Reynolds, J. E. F. and Prasad, A. B., The Pharmaceutical Press, London, 1982, pp. 862–864). Additional pronounced counter irritating activity of iodine was demonstrated against skin irritation caused by chemical and thermal stimuli. Post-exposure treatment with topical povidone-iodine preparation resulted in significant protection against mustard gas (sulfur mustard, SM) -induced skin lesions (Wormser et al. Arch. Toxicol. (1997) 71, 165–170). High degree of protection was achieved at intervals of 5 and 10 minutes between exposure and treatment, whereas at 20 minutes interval iodine had much weaker effect. Iodine was also effective against other skin irritants such as mechlorethamine, divinylsulfone, iodoacetic acid and cantharidine (Wormser et al. Arch. Toxicol. (1997) 71, 165–170). Additional studies have shown the counter-irritating activity of povidone-iodine against thermal stimuli in humans (Wormser, Burns (1998) 24, 383). The experience with patients after accidental heat burns (mostly of grade I; caused by hot water or oil or by hot steam) has shown that topical application of povidone-iodine ointment immediately after the stimulus reduced the degree of skin lesions. The shorter the interval between stimulus and treatment the better was the protection achieved, namely, more than 3 minutes after the heat stimulus the povidone-iodine preparation may not be of significant help (Wormser, Burns (1998) 24, 383).

Iodine is an essential trace element in the diet. Deficiency of iodine may lead to development of goiter. The adult minimum daily requirement is 100 µg which should be supplied via the diet or drinking water (Martindale, The extra pharmacopoeia, 28th edition, Eds.: Reynolds, J. E. F. and Prasad, A. B., The Pharmaceutical Press, London, 1982, pp. 862–864). Iodine and iodide are used in conjunction with antithyroid agents in the preoperative treatment of thyrotoxicosis. The patient is rendered euthyroid with an antithyroid agent and iodine or iodides are then added to the therapy for about 10–12 days before thyroidectomy. Treatment with iodine or iodides may be continued post-operatively as well. Aqueous iodine solutions are used for these kinds of treatments (Martindale, The extra pharmacopoeia, 28th edition, Eds.: Reynolds, J. E. F. and Prasad, A. B., The Pharmaceutical Press, London, 1982, pp. 862–864).

Molecular iodine ($I_2$) is practically water insoluble unless iodide (sodium or potassium salts) is present in the solution to form the water soluble ion $I_3^-$. Iodine can be dissolved in ethanol but the presence of water precipitates the iodine, thus iodine tincture (which contains ethyl alcohol and water) must also contain iodide to form $I_3^-$ for proper dissolution. Polyethyleneglycol-400 may also solve $I_2$ but the presence of water precipitates the iodine. Incubation at room temperature for about 24 hours dissolves the precipitate, however, as will be shown later, this formulation is less effective than the proposed iodine formulation. Apart from being unsuitable for topical use, other organic solvents, capable of solving iodine such as carbon tetrachloride, diethyl ether, or chloroform are not miscible with water and cannot form an aqueous solution.

The negative charge of $I_3^-$ may restrict its penetration through biological membranes and barriers, thus, its efficacy as an antiseptic agent or counterirritant is limited. Nevertheless, a solvent system that might solve $I_2$ without addition of iodide, thus keeping the molecular iodine in its non-charged form i.e. $I_2$, is more penetrable and possesses stronger chemical activity as an oxidizer, and therefore is more efficient in both its antiseptic and counter irritating activities.

The present invention provides a new iodine ($I_2$) formulation composed of solid iodine dissolved in tetraglycol (glycofurol, tetrahydrofurfuryl alcohol polyethyleneglycol ether) (TG), wherein said iodine can be present at a concentration relative to the entire formulation of between 0.00001 and 50%. Water may be added without affecting the solubility of iodine in TG and thus said composition can further comprise an aqueous diluent whereby TG can be present at a concentration of between 1 and 100% relative to the entire formulation. For ointment preparation a polymer (for example poloxamer 407) and/or a phospholipid (lipoid 75-3) may be added.

In fact, iodide-containing preparations (such as 2% $I_2$, 2.4% NaI, 47% ethanol, water up to 100%) were less effective than preparations in which iodine was dissolved in TG.

It is noteworthy that iodine can be dissolved (2% concentration) in polyethyleneglycol (PEG)-400. This formulation has also counter-irritating activity against SM. In the presence of water iodine precipitates and dissolves again after overnight incubation at room temperature. However; the counter-irritating activity of the water containing PEG formulation is much weaker than that of TG:water 50%:50%.

According to the present invention povidone-iodine polyvinylpyrrolidone-iodine complex) (PVP-I) is also dissolved in TG or a TG water system, thus, similar uses and formulations can be applied to PVP-I. In fact, PVP-I was less effective than $I_2$ (both oxidizers dissolved in TG and water) against chemical and thermal burns in the haired guinea pig skin model.

The above mentioned studies concerning skin counter irritation were performed with a commercial povidone-iodine preparation composed of water, polyethylene glycols and buffering system. As mentioned above, the protective effect of this preparation against mustard gas within 10 minutes after exposure and to a lesser extent at interval of 20 minutes between exposure and treatment. Other formulations of povidone iodine or iodine were not proved to be more effective. However, post-exposure treatment with the compositions according to the present invention significantly protected against mustard gas-induced chemical burns at interval of 15 and 30 min between exposure and treatment. Some degree of protection, albeit lower than the shorter intervals, was achieved at longer interval such as 45 min between exposure and treatment and even at 60 min interval some degree of protection was observed.

The superiority of the counter irritating effect of the compositions according to the present invention was also proved in thermal burns. The currently available formulation of povidone iodine was shown to be effective in humans provided the affected skin was treated within 2–3 min after heat exposure (Wormser, Burns (1998) 24, 383). However, the compositions according to the present invention showed stronger counter-irritating activity against thermal stimuli with interval of 8 min between exposure and treatment (a case study). In addition, animal experimentation demonstrated the protective effect of the compositions according to the present invention against thermal stimuli whereas various povidone iodine preparations were ineffective in experimental animals.

The present formulation has more potent antiseptic properties than the currently available commercial iodine preparations, namely, the bacteria killing effect requires lower iodine concentrations while using the compositions according to the present invention relatively to the available formulations. This effect was tested on various types of bacteria.

The present invention relates to TG as a vehicle of molecular iodine and/or as a component in iodine formulation. The present invention relates to TG as a vehicle of iodine as molecular iodine ($I_2$), but also as a vehicle of iodine-containing and especially $I_2$—releasing preparations, including but not limited to, povidone iodine, in which iodine or iodide is not covalently bound to a molecule or macromolecule.

The counter-irritating properties of the compositions according to the present invention can be employed, as prophylactic and post-exposure treatments, against all kinds of factors causing damage to skin, eye, and mucus tissues. In addition to the above mentioned protecting effect against chemical and heat burns, the compositions according to the present invention can be used against all kinds of skin irritating factors such as chemicals including acids, bases, nitrogen mustards, alkylators such as cantharidine, and iodoacetat, corrosive chemicals, detergents; extreme temperatures including hot metal, wood, plastic, water, oil, steam, and gas, fire, low temperature caused by cold weather, liquid gas such as air and nitrogen; all kinds of irradiation sources including ionizing and ultraviolet A, B, and C irradiation; all kinds of mechanical irritation; irritating factors of biological and/or natural origin including bacteria, viruses, fungi, prions, micoplasma and all kinds of parasites, protozoa, metazoa. The counter-irritating activity of the compositions according to the present invention can also be beneficial in a variety of skin diseases including psoriasis, acne, various kinds of dermatitis and eruptions. It may also be used for treatment of irritation and diseases of eye and mucus tissues.

The compositions according to the present invention may be used for facilitating healing processes of skin, eye, and mucus tissues. Topical treatment with the compositions according to the present invention can be employed for shortening healing process of damaged tissue caused by various irritating factors or by pathogenic agents.

In addition to be topically used in mucous membranes, iodine was reported to be topically applied as counter-irritant in rheumatism, tenosynovitis and in the treatment of inflammatory diseases of the peripheral nervous system and muscles ((Martindale, The extra pharmacopoeia, $28^{th}$ edition, Eds. Reynolds, J. E. F. and Prasad, A. B., The Pharmaceutical Press, London, 1982, pp. 862–864). Due to its advantages over other preparations, the compositions according to the present invention can be efficiently employed for treatment of such disorders as well.

The compositions according to the present invention can be employed as antiseptic agent as described in the examples herein. The formulation can be used as a component of tooth paste and/or mouth wash as well. The formulation can also be a disinfectant of drinking water. It might also be useful in as protectant in case of exposure to radioactive isotopes ($^{125}$I, $^{131}$I).

In summary, the compositions according to the present invention can be used in the various medicinal disciplines including human and veterinary medicine. More generally, the compositions according to the present invention can be used in each case that iodine is involved including, but not limited to, medicine, industrial processes supplemental in diet, diagnostics and environmental purposes.

Thus, the present invention provides a system containing molecular iodine or compounds releasing molecular iodine in concentrations of between 0.00001%–50% $I_2$ and TG in a concentration of between 1 and 99% in an acceptable vehicle, especially in a pharmaceutically acceptable vehicle.

The pharmaceutically acceptable vehicle is preferably selected from the group consisting of an oil/water or a water/oil emulsion, a solution, a suspension, a gel, an ointment, a patch, or an aerosol. The preferred vehicle is selected from the group consisting of solutions, gels and washable ointments.

In embodiments wherein the composition is a gel or a washable ointment, the gelling agents are preferably selected from the group consisting of polysaccharides, such as cellulose derivatives, acrylic polymers, proteins, polyvinyls, such as polyvinyl pyrrolidone (povidone), polyvinyl alcohol, polyhydroxy compounds, such as poloxamers, polyethlene glycols (PEG), and macromolecules consisting of PEG and fatty alcohols, such as cetostearyl alcohol, in their molecular structures. The preferred gelling agents are polyvinyl alcohols and poloxamers.

In preferred embodiments of the present invention said molecular iodine is released from an iodine-containing and/or producing agent preferably selected from the group consisting of cadexomer-iodine, diiodhydrin, domiodol, hydriodic acid, iodinated glycerol, iodoform, and povidone-iodine.

While the invention will now be described in connection with certain preferred embodiments in the following examples and with reference to the accompanying figures so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

BRIEF DESCRIPTION OF THE DRAWINGS

In the drawings:

FIG. 16: is a graphic representation of the effect of different iodine concentrations against UV irradiation (30 min prophylaxis; and.

EXAMPLE 1

Figure 1:
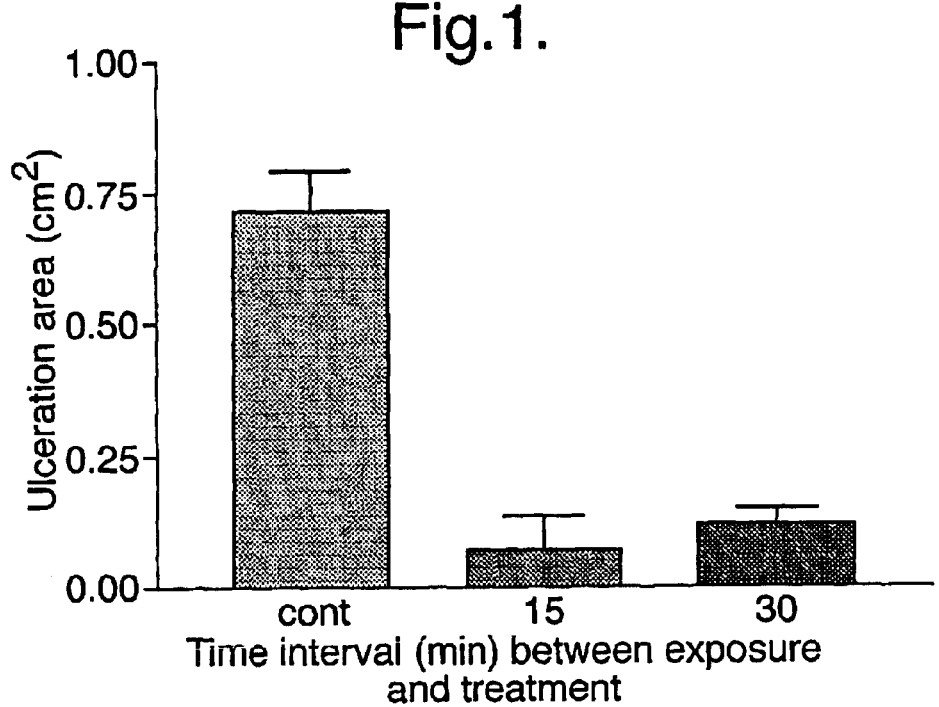
FIG. 1 is a graphic representation of the protective effect of iodine against SM-induced skin.

Protective Effect of Iodine Against Sulfur Mustard (SM)-Induced Skin Burns in Haired Guinea Pig Model Experimental Procedure:

Backs of haired guinea pigs (male, Dunken Hartley, 650–850 g) were shaved 24 hours prior the experiment. The animals were anesthetized by 30 mg/kg pentobarbital sodium ip. Backs were cleaned with wet soft white paper and let to dry out before the beginning of experiment. Six sites (three on each side) of each back were exposed to 1 $\mu$l (1.2 mg) SM. One ml liquid iodine (2% in TG:water 1:1) was applied on three exposure sites of each animal while the other 3 SM-exposed sites of each animal remained untreated (control). Iodine was applied into wells that constructed by the following procedure. A plastic tube cover (inner diameter of 1.7 cm) was cut to form open-ended cylindrical well and a thin layer of commercial silicon sealing ointment was applied to one edge of the well. The well was then attached to the animal back so liquid inside the well did not leak out. In all cases of iodine treatment, wells were constructed before exposure while SM was applied on the center of the well. At the indicated time intervals after exposure (numbers below bars) iodine was applied for 2 hours. In the end of the procedure the liquid iodine was sucked out and well removed from the skin. Digital camera photos were taken after 2 days and the lesions were evaluated by mean of area of ulceration. In general, each experiment composed 8 guinea pigs of which 2 were pure controls, namely, all 6 application sites were not treated with iodine, and 6 animals were SM-exposed and iodine-treated as described above. Results are expressed as mean±SEM using the non parametric Kruskal Wallis test and Dunnett's multiple comparison post test for statistical evaluation of the difference between control (SM only) and iodine-treated skin. Numbers of the tested skin pieces were as follows: SM only (n=59); time interval between exposure and treatment of 15 min (n=9) and 30 min (n=18).

Results: FIG. 1 shows that post-exposure treatment with iodine-TG (2% $I_2$ in TG/water 1:1) preparation reduced the ulceration area caused by SM as compared to the non-treated area. At time intervals of 15 and 30 min between exposure and treatment the ulceration area was reduced by 90.7% (p<0.001) and 84% (p<0.001), respectively.

EXAMPLE 2

Effect of Duration of Iodine Treatment on the Degree of Protection in the Haired Guinea Pig Model The experimental procedure was similar to that described in Example 1 with the following modifications. The interval between SM exposure and iodine treatment was 30 min. Liquid iodine (2% in TG:water 1:1) was left in the well for the indicated time intervals, then, the liquid was sucked out and wells were removed. Photos and assessment of area of ulceration were taken 5 days after treatment. Difference between 180 min treatment and control (SM only) was evaluated by Mann-Whitney test. Numbers on columns indicate number of tested skin pieces.-

Figure 2:
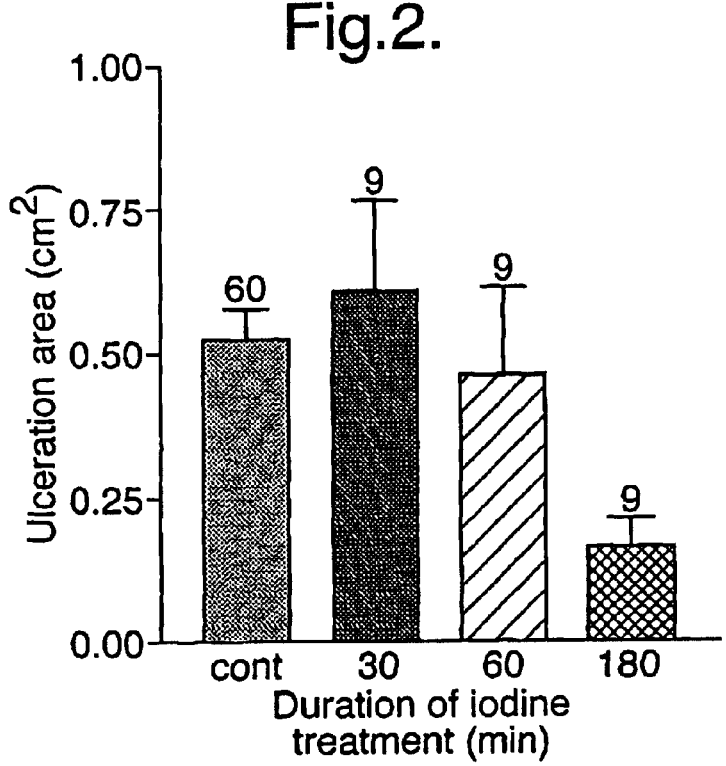
FIG. 2 is a graphic representation of the effect of the duration of iodine application on the protective effect against SM skin toxicity.

Results: Iodine left on the skin for 3 hours showed significant protection against SM (p=0.011) (FIG. 2). From example 1 it can be shown that, for significant protection, iodine should be left for at least 2 hours in the haired guinea pig skin model.

EXAMPLE 3

Figure 3:
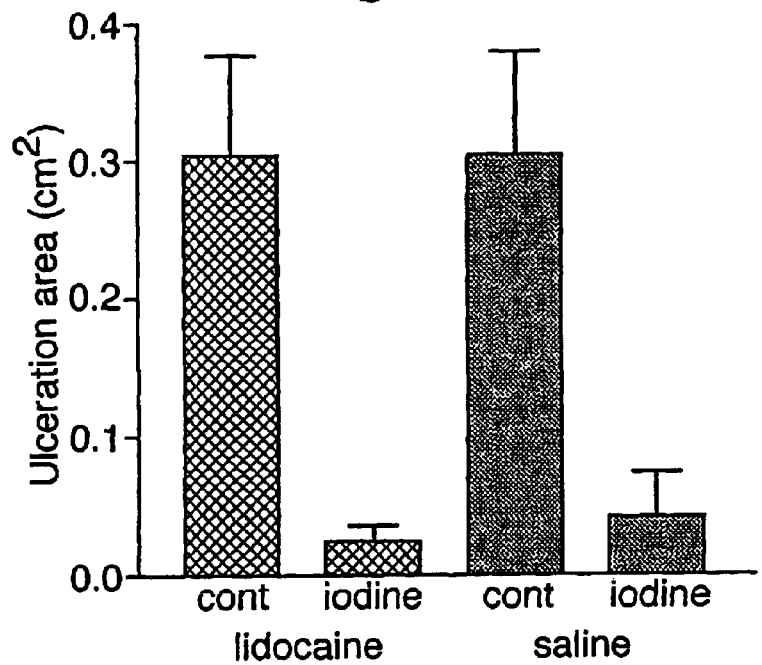
FIG. 3 is a graphic representation of the effect of lidocaine on iodine-induced protection against SM skin toxicity.

Effect of Lidocaine on the Protective of Iodine Against SM-Induced Skin Lesions in the Haired Guinea Pig Model The experimental procedure was similar to that described in Example 1 with the following modifications. Twenty minutes prior SM application, each site of exposure was s.c.injected with lidocaine (0.1 ml of 2% solution). Site of injection was located about 1 cm laterally to the site of SM exposure. The control group was s.c. injected with saline. Iodine ointment preparation (2% $I_2$, 50% TG, 20% Poloxamer-407, 28% water) was applied 15 min after SM exposure without well construction. Photos and assessment of area of ulceration were taken 7–10 days after treatment. Difference between iodine treatment and control (SM only) was evaluated by Mann-Whitney test.
Results: There was a statistically significant difference in the ulceration area between SM only and SM followed by iodine treatment in both lidocaine (p<0.0001) and saline (p=0.0052) injected animals (FIG. 3). Lidocaine by itself had no effect on the protective effect of iodine.

EXAMPLE 4

Figure 4:
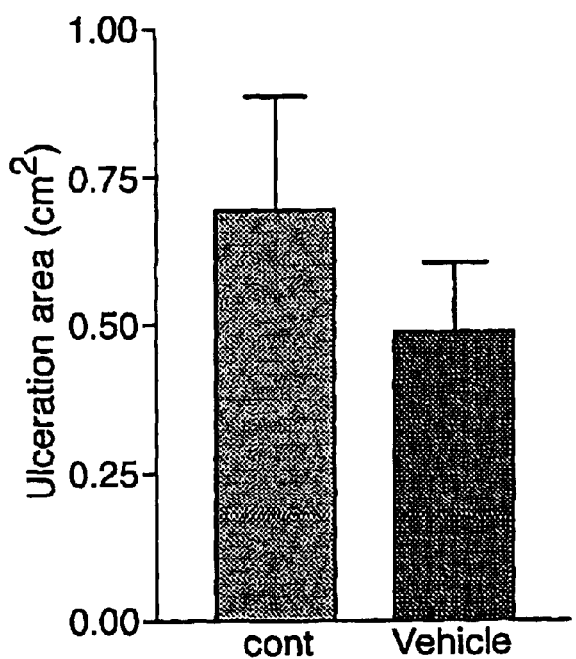
FIG. 4 is a graphic representation of the effect of the iodine vehicle on SM induced skin toxicity.

Effect of the Iodine Vehicle on SM-Induced Skin Toxicity in the Haired Guinea Pig Model The experimental procedure was similar to that described in Example 1 with the following modifications. The vehicle (TG:$H_2O$, 1:1) was applied into the well 15 min after SM exposure. Two hours later the vehicle was sucked out and wells were removed. Photos for evaluation of ulceration area were taken 4–6 days after exposure.
Results: There was non statistically significant reduction of 30% in ulceration area caused by the vehicle (FIG. 4) as compared to the control (SM only). That means that the vehicle has some protective effect against SM but the main effect is attributed to the presence of iodine as showed in the above mentioned examples.

EXAMPLE 5

Protective Effect of Iodine Against Vapor SM in the Hairless Guinea Pig Model

Figure 5:
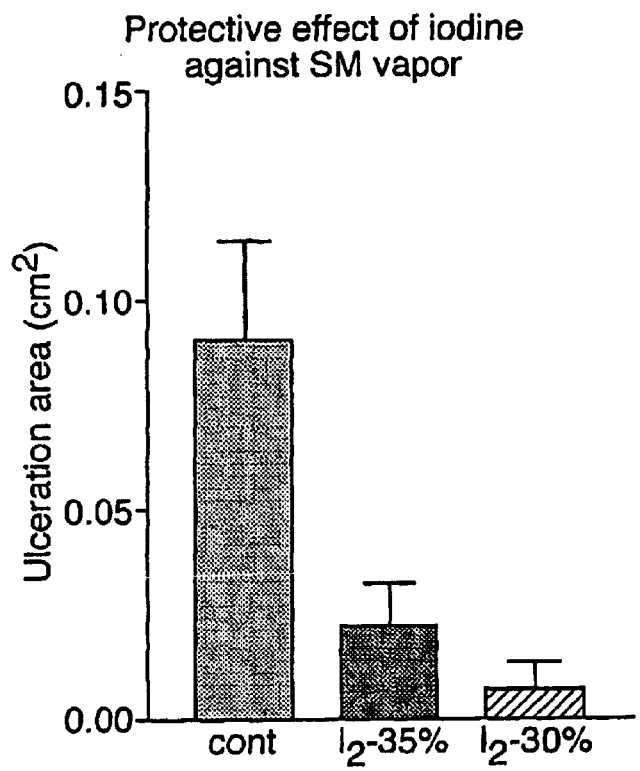
FIG. 5 is a graphic representation of the protective effect of iodine against vapor SM.

Hairless guinea pigs were anesthetized as described in example 1. Six sites on each back were exposed to vapor SM by the following procedure. A Whathman N1 filter paper disk (1.0 cm diameter) was put on the inner side of the base of a plastic tube cork. The edges of the open-ended side of the cork were applied with a commercial sealing ointment. Then, 10>|SM were applied on the paper and the open-ended side of the cork was attached to the skin. The cork was removed after 16 min followed by iodine ointment application. The formulations used in this study were as follows:
a) $I_2$-35%: 2% $I_2$50% TG, 35% poloxamer-407, 1% lipoid 75-3, 12% water;
b) $I_2$-30%: 2% $I_2$50% TG, 30% poloxamer-407, 1% lipoid 75-3, 17% water. Photos for evaluation of ulceration area were taken 3 days after exposure.
Results: There was a reduction of 75% and 93% in the ulceration area after treatment with ointment containing 35% and 30% poloxamer-407, respectively. Although both results are not statistically different from the control (burn without iodine treatment), there is a trend which markedly indicates for the beneficial effect of the iodine preparations (FIG. 5).

EXAMPLE 6

Figure 6:
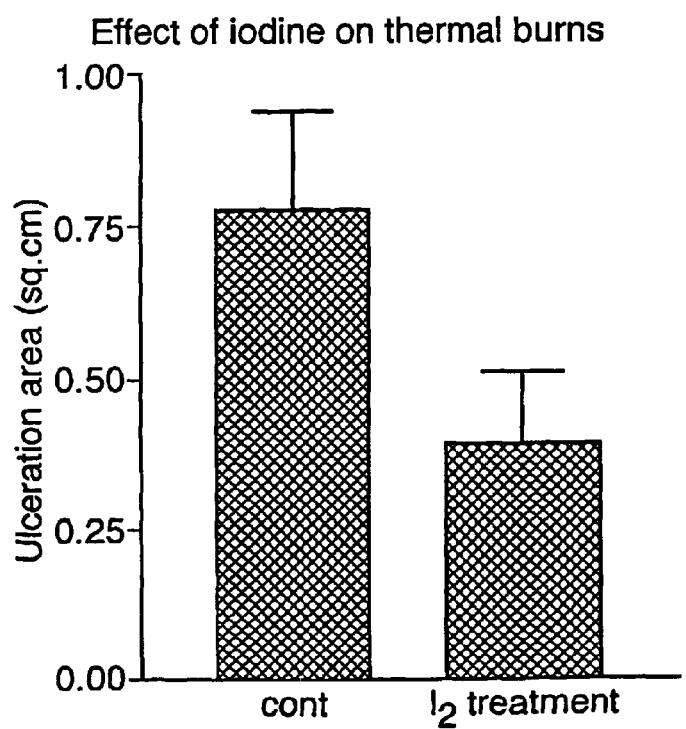
FIG. 6 is a graphic representation of the protective effect of iodine against thermal burns.

Protective Effect of Iodine Against Thermal Burns in the Haired Guinea Pig Model The back of guinea pig was depilated 24 hours prior the experiment. The skin area was applied with white soft paraffin immediately after depilation. Anesthesia and well construction was carried out as described in Example 1 except of the fact that six well were constructed on each back. Water (2.0 ml) at 90° C. poured into each well and after 10 sec sucked out. Immediately thereafter 1 ml iodine formulation (2% in TG:$H_2O$ 1:1) was poured into 3 wells whereas the other 3 sites of exposure remained untreated (controls). Two hours later, iodine was sucked out and wells were removed. Photos for evaluation of ulceration area were taken after 2 days.
Results: There was reduction of 50% in the ulceration area of iodine-treated burns as compared to the control group (FIG. 6). Although not statistically significant from control (burn without iodine treatment) there is strong indication for the protective effect of iodine against heat burns.

EXAMPLE 7

Protective Effect of Iodine Against Thermal Burns in Human-a Case Report

A 9 years old girl was exposed by accident to liquid soup of about 75–80° C. Exposure took place in the dorsal side of the femur (area of 4×4 cm) and on the ventral side of the forearm 8 cm from the wrist (about 4×4 cm). The patient suffered from strong burning sensation and severe erythema at sites of exposure. About 10 min after exposure the femur skin was topically applied with iodine ointment (2% $I_2$, 50% TG, 30% Poloxamer-407, 1% lipoid 75-3, 17% water) and the forearm with iodine ointment (2% $I_2$, 50% TG, 35% Poloxamer-407, 1% lipoid 75-3, 12% water). Two to three minutes after iodine application both femur and forearm burning sensation stopped, and about 30 min later the ointment was removed and both skin areas seemed normal without toxicity signs. Follow up during the next days did not show changes.

EXAMPLE 8

Antiseptic Effect of the New Iodine Formulation

Iodine has been used for a long time in the form of tincture of iodine or Lugol's solution for the topical antiseptic treatment of wounds. However, its efficacy in these formulations has not been thoroughly examined and established. We examined these formulations as compared to our new formulation. Minimum inhibitory concentration (MIC) measurements of various iodine formulations were performed with *E. coli*, *Bac. Subtilis*, and *Ps. Putida*.

FIGS. 7–11 demonstrate the beneficial inhibitory effect of the presently claimed new product over a tincture or a solution of iodine at the same concentration.

The test compositions of Example 8 (quantities in grams)

| Ingredients | Formulation 1 2% new | Formulation 2 2% tincture | Formulation 3 2% solution | Formulation 4 10% PI new | Formulation 5 "Polydine"* |
|---|---|---|---|---|---|
| Iodine | 2.0 | 2.0 | 2.0 | 10.0 | 10.0 |
| TG | 50.0 | — | — | 50.0 | — |
| Na$_2$HPO$_4$ × 12H$_2$O | 0.3 | — | — | — | — |
| Ethanol | — | 37.6 | — | — | — |
| NaI | — | 2.4 | 4.0 | — | — |
| PEG 400 | — | — | — | — | + |
| Water | 48.0 | 58.0 | 94.0 | 40.0 | + |

*Commercial solution (Fischer Ltd., Israel), Lot 362378, Exp. 07/03

Figure 7:
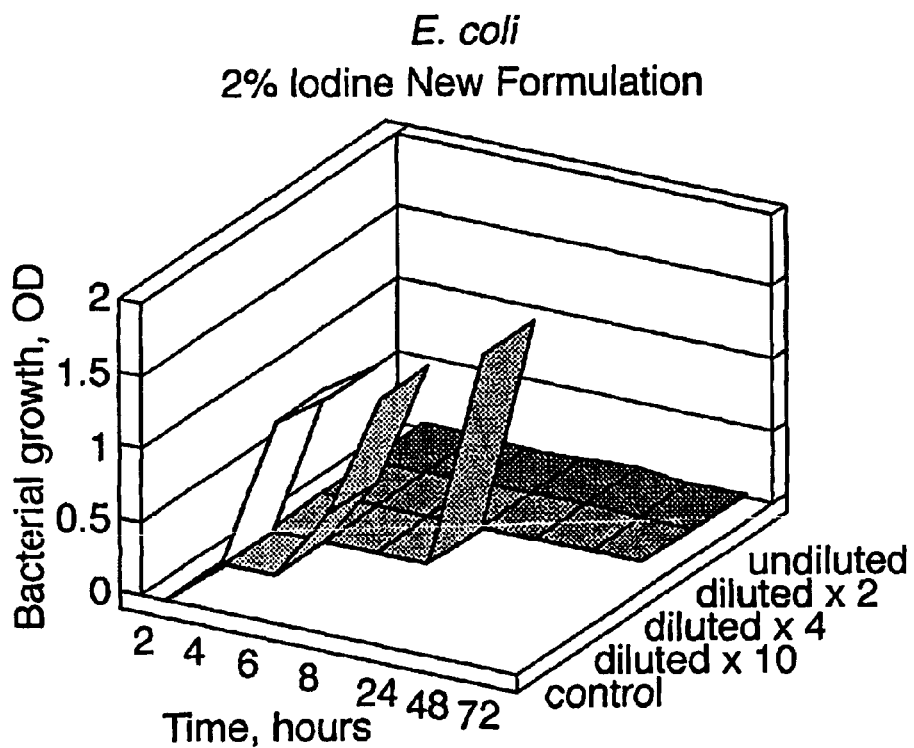
FIG. 7 is a graphic representation of the MIC of a 2% iodine in the compositions of the present invention containing TG vis-a-vis *E. coli, Bacillus subtilis* and *Ps. putida;*
Figure 7:
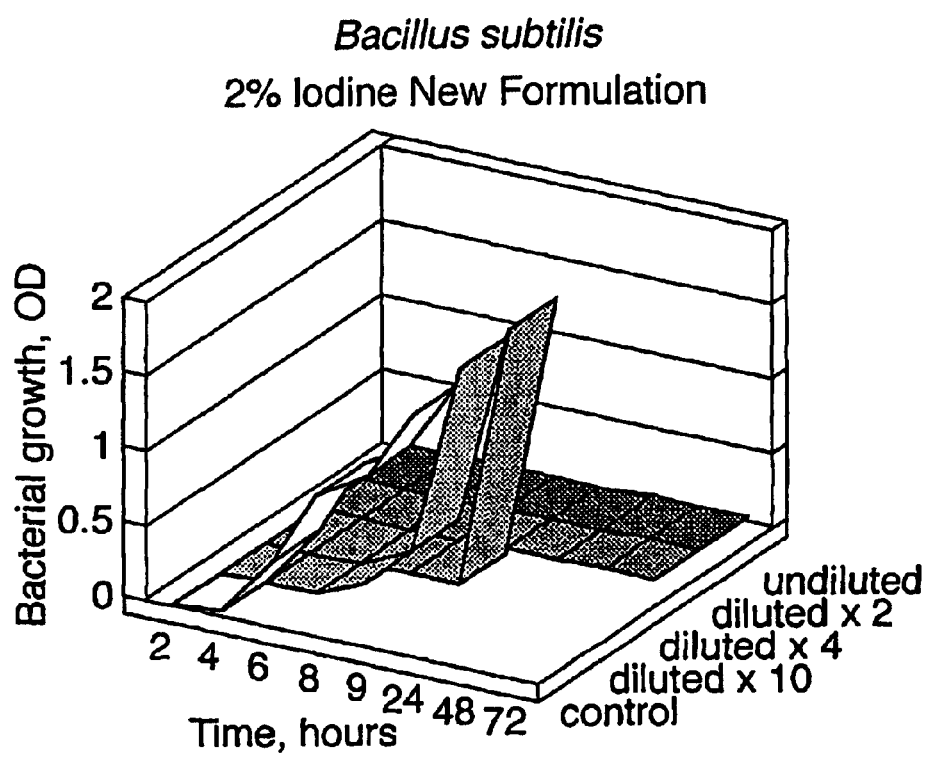
Figure 7:
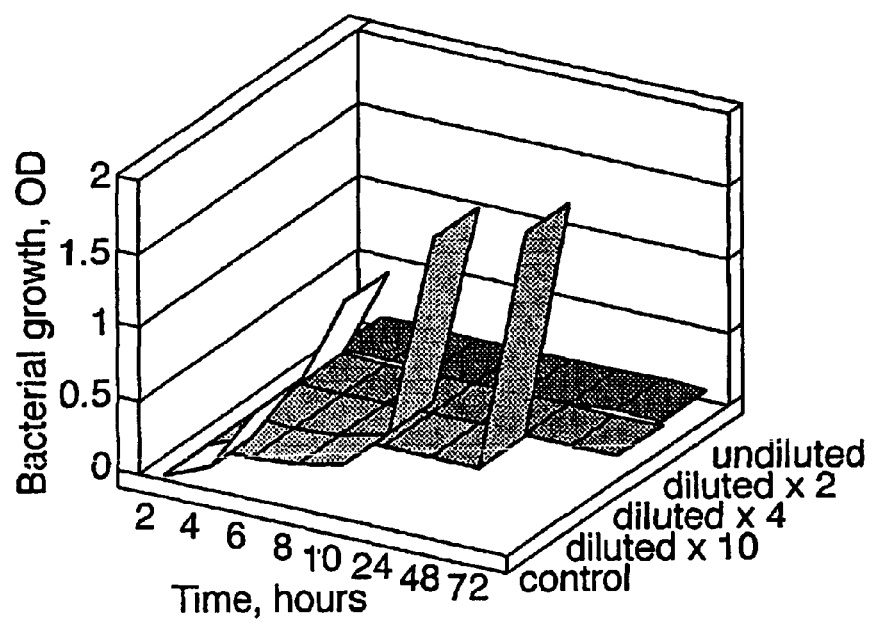
Figure 7A:
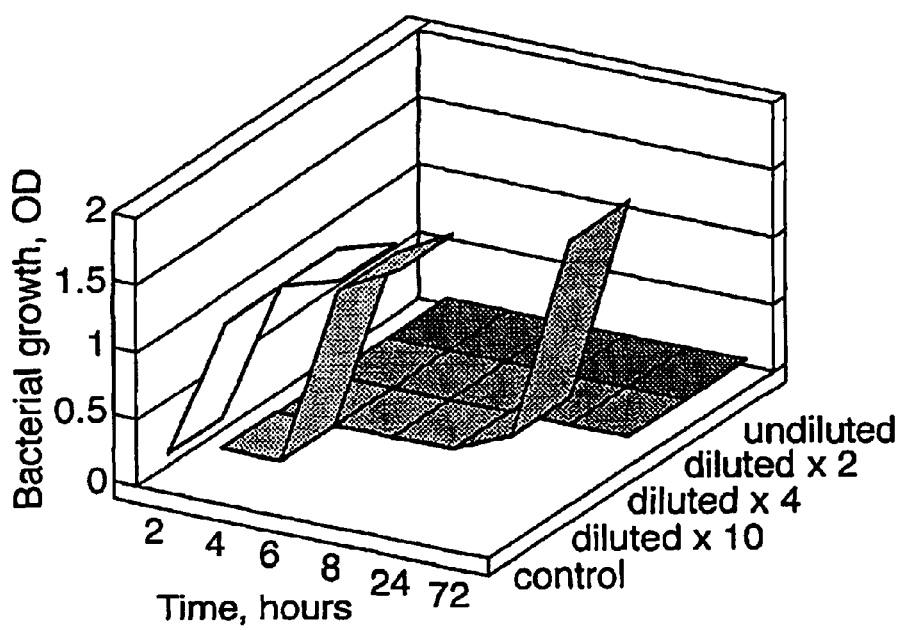
FIG. 7a is a further graphic representation of the MIC of a 2% iodine in the compositions of the present invention containing TG vis-a-vis *E. coli, Bacillus subtilis* and *Ps. putida;*
Figure 7A:
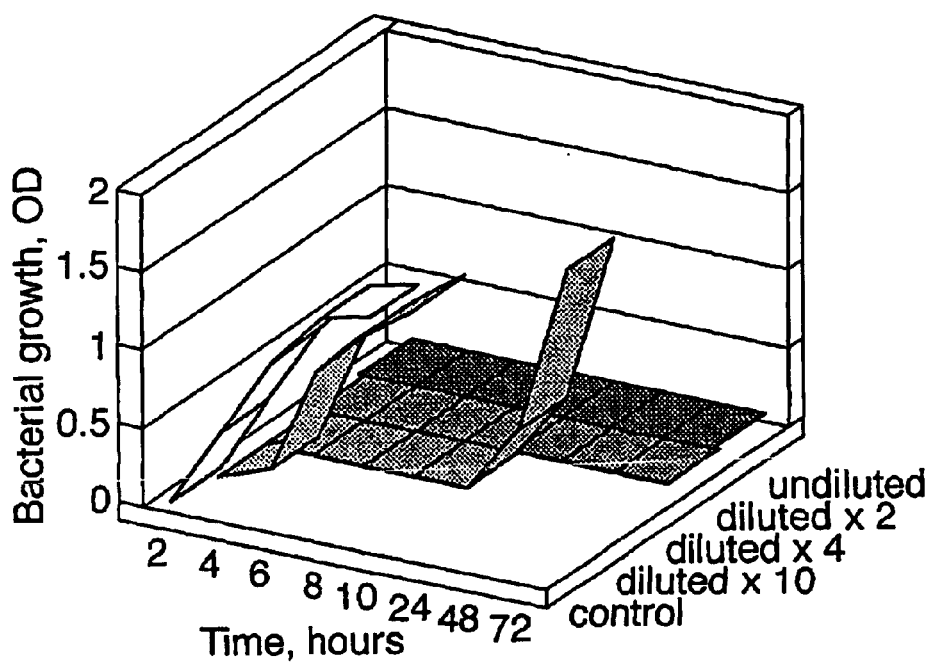
Figure 7A:
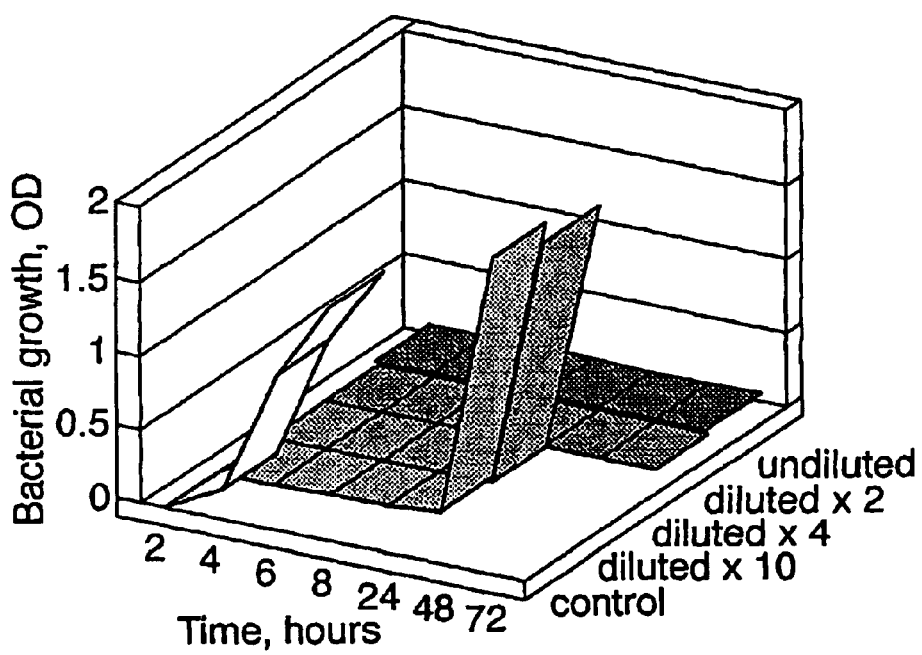
Figure 8:
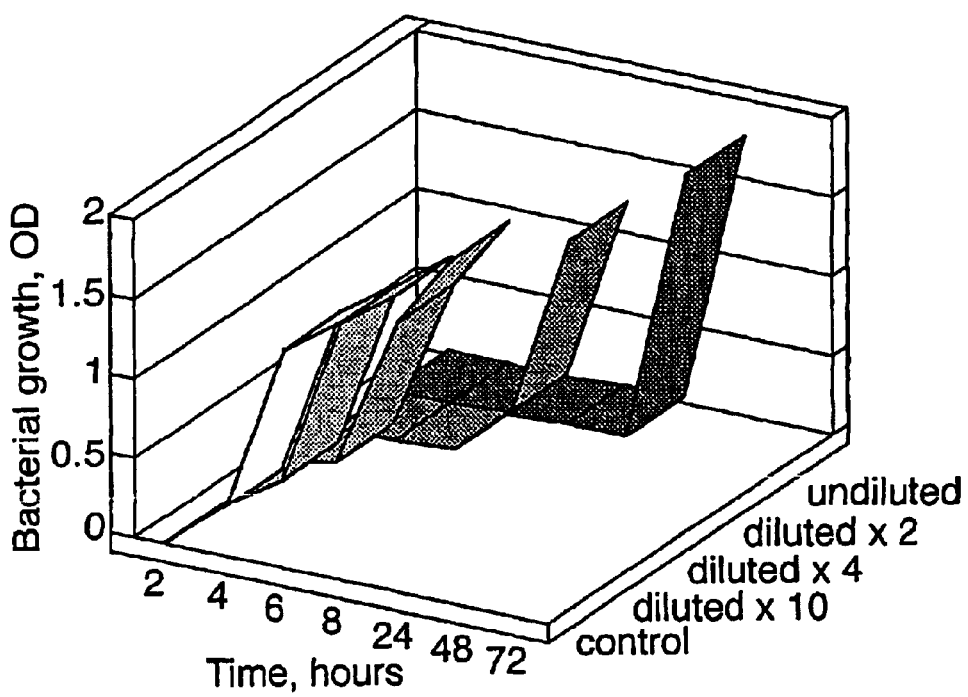
FIG. 8 is a comparative graphic representation of the MIC of a 2% iodine in ethanol vis-a-vis *E. coli, Bacillus subtilis* and *Ps. putida;*
Figure 8:
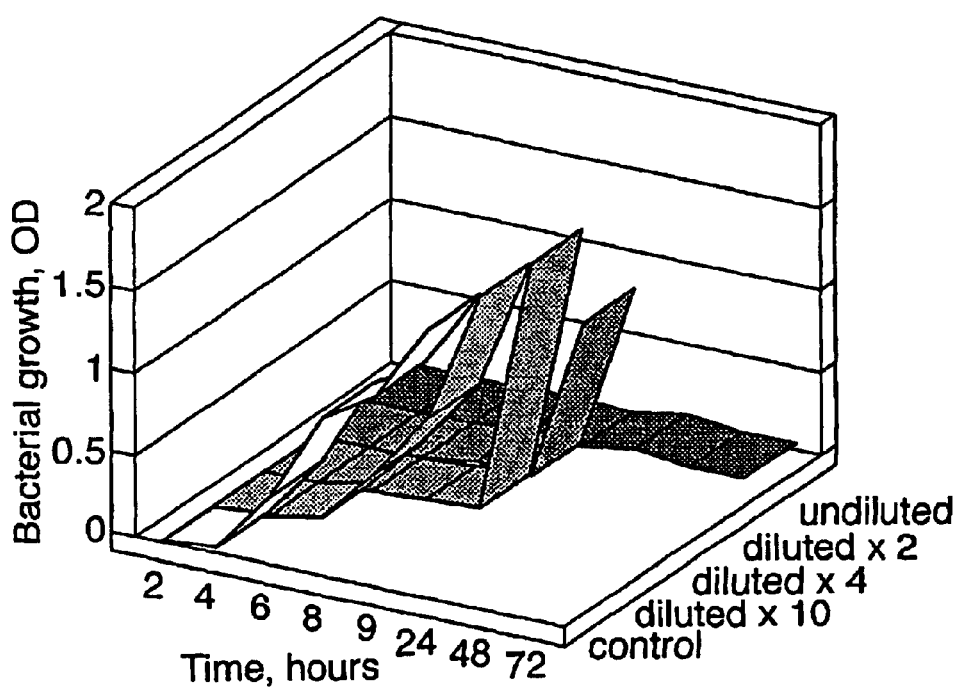
Figure 8:
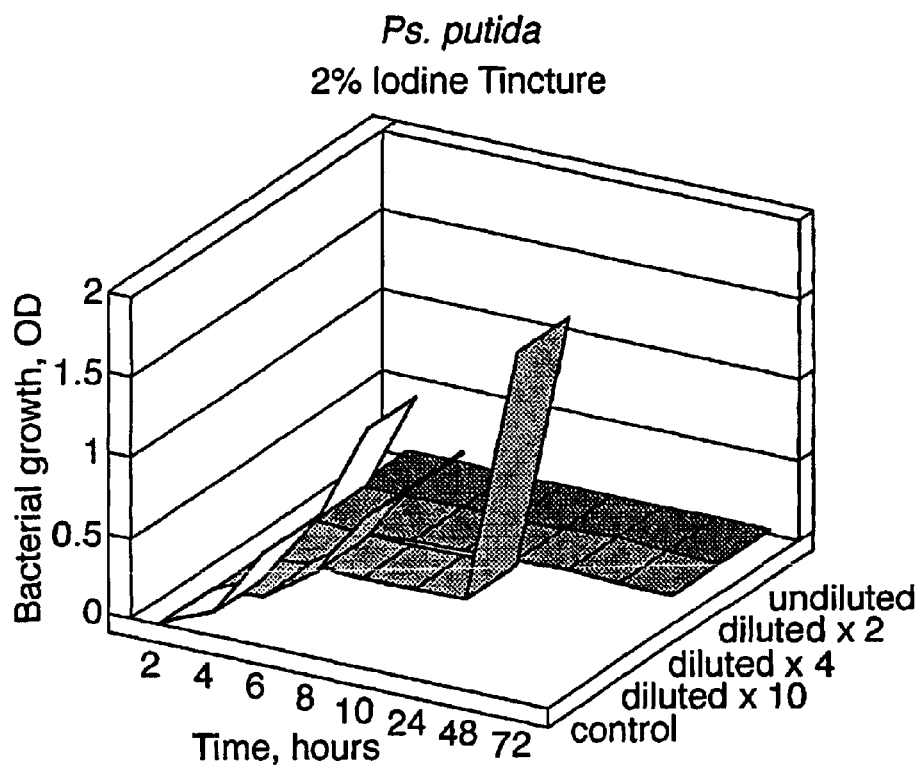
Figure 9:
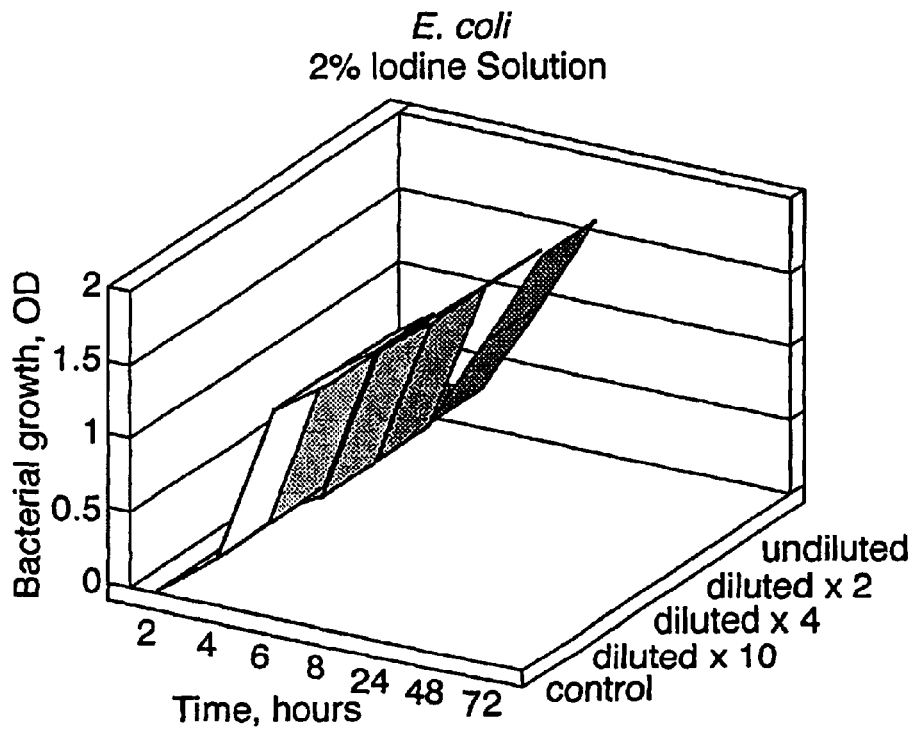
FIG. 9 is a graphic representation of the MIC of a 2% aqueous composition containing NaI vis-a-vis *E. coli, Bacillus subtilis* and *Ps. putida;*
Figure 9:
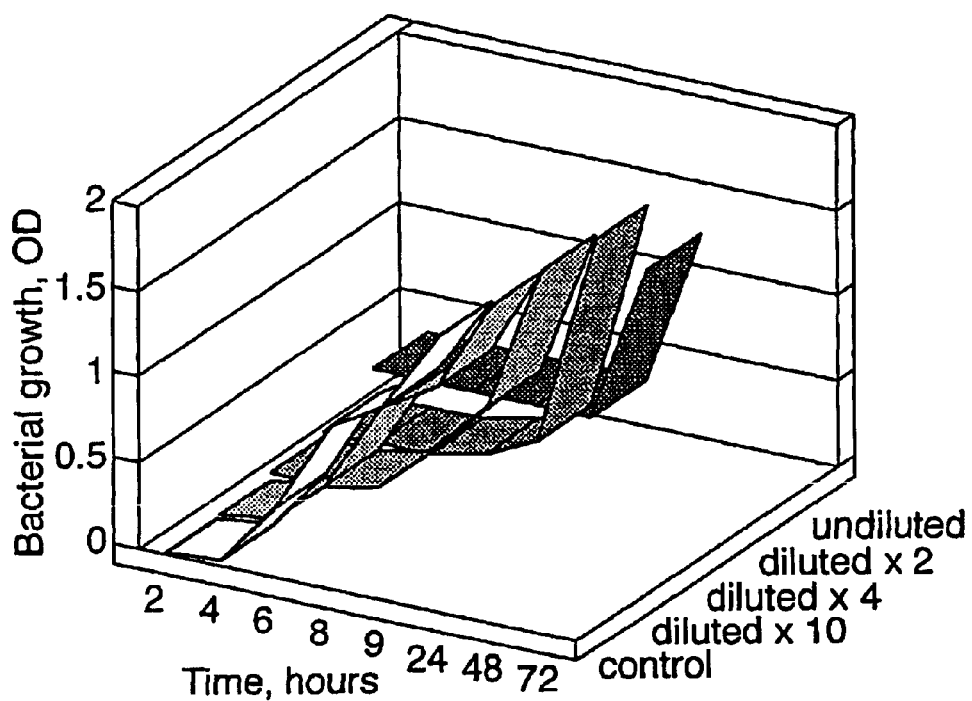
Figure 9:
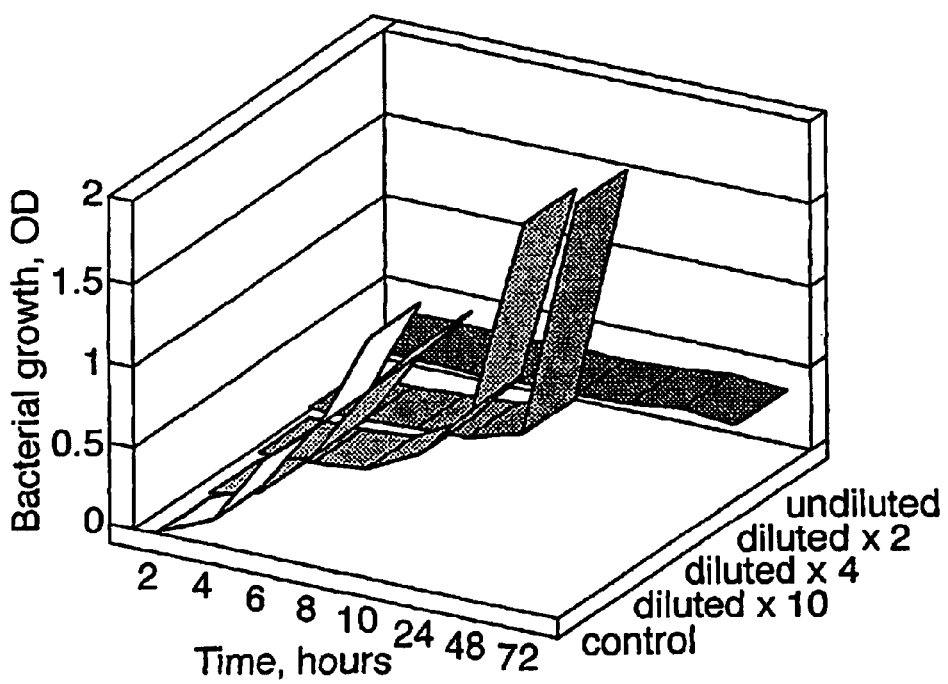
Figure 10:
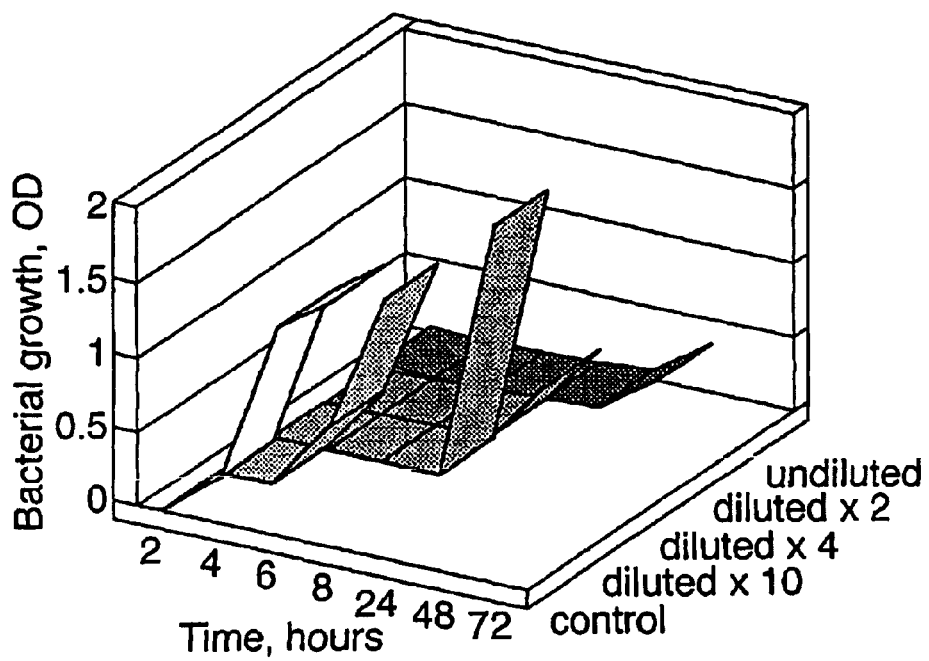
FIG. 10 is a graphic representation of the MIC of iodine in a 10% povidone-iodine composition of the present invention containing TG vis-a-vis *E. coli, Bacillus subtilis* and *Ps. putida;*
Figure 10:
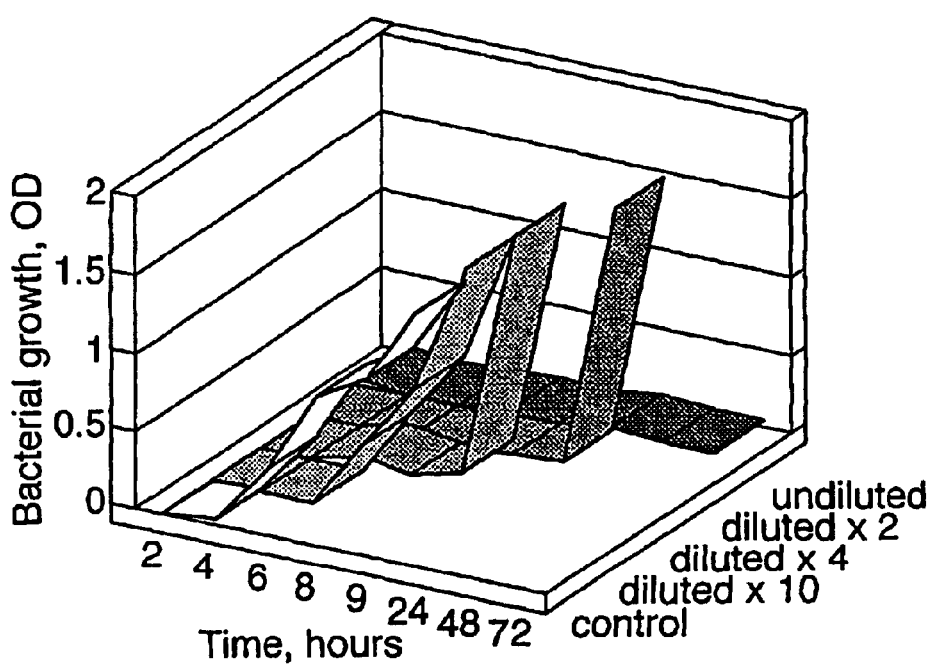
Figure 10:
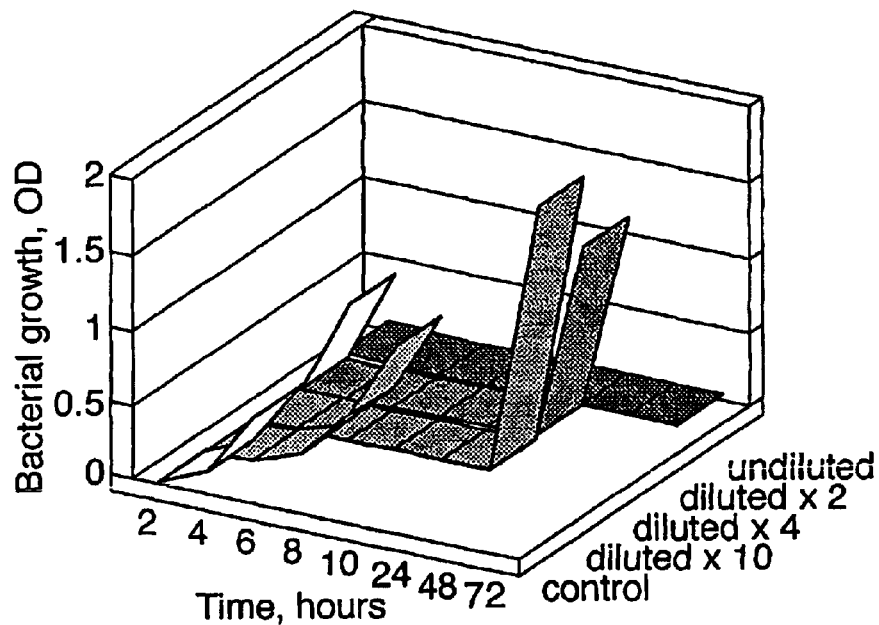
Figure 11:
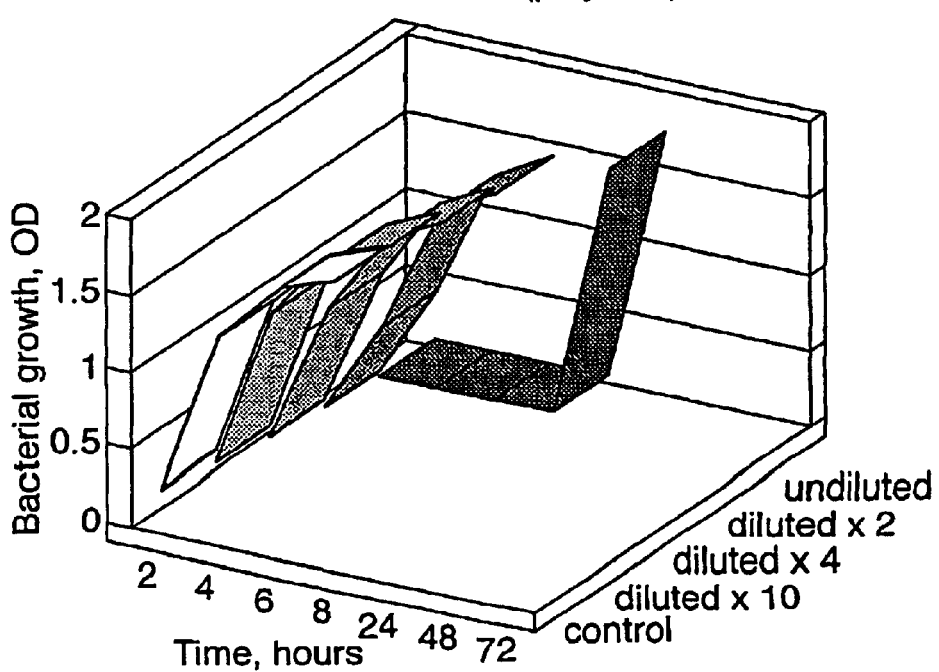
FIG. 11 is a comparative graphic representation of the MIC of a 10% povidone-iodine composition containing PEG vis-a-vis *E. coli, Bacillus subtilis* and *Ps. putida;*
Figure 11:
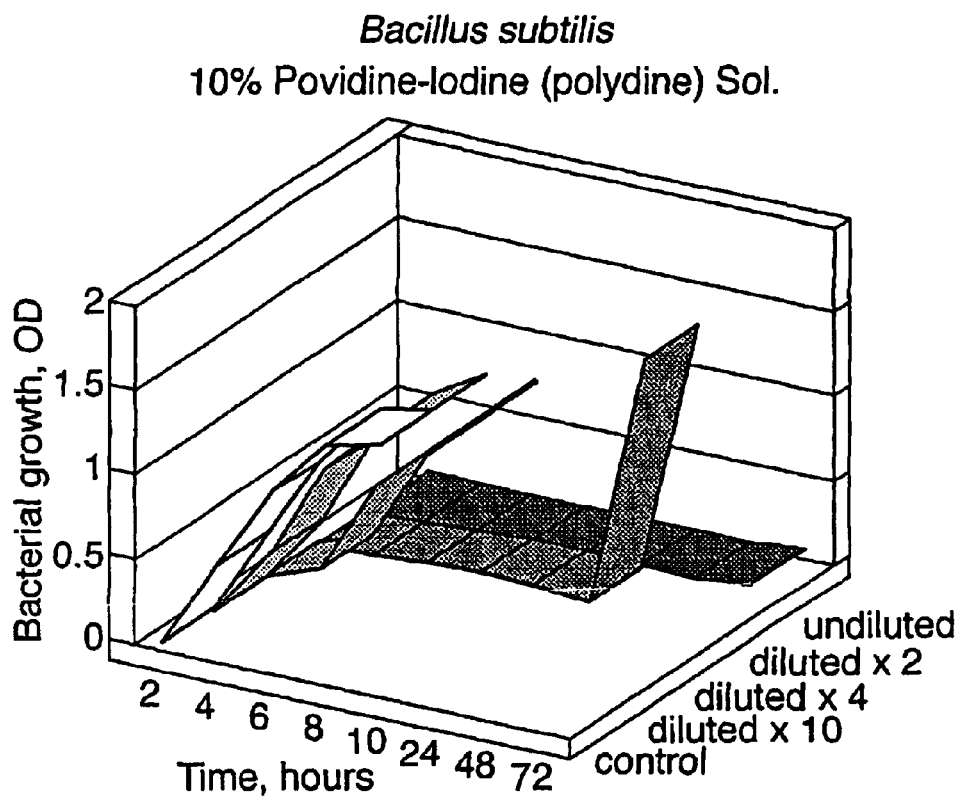
Figure 11:
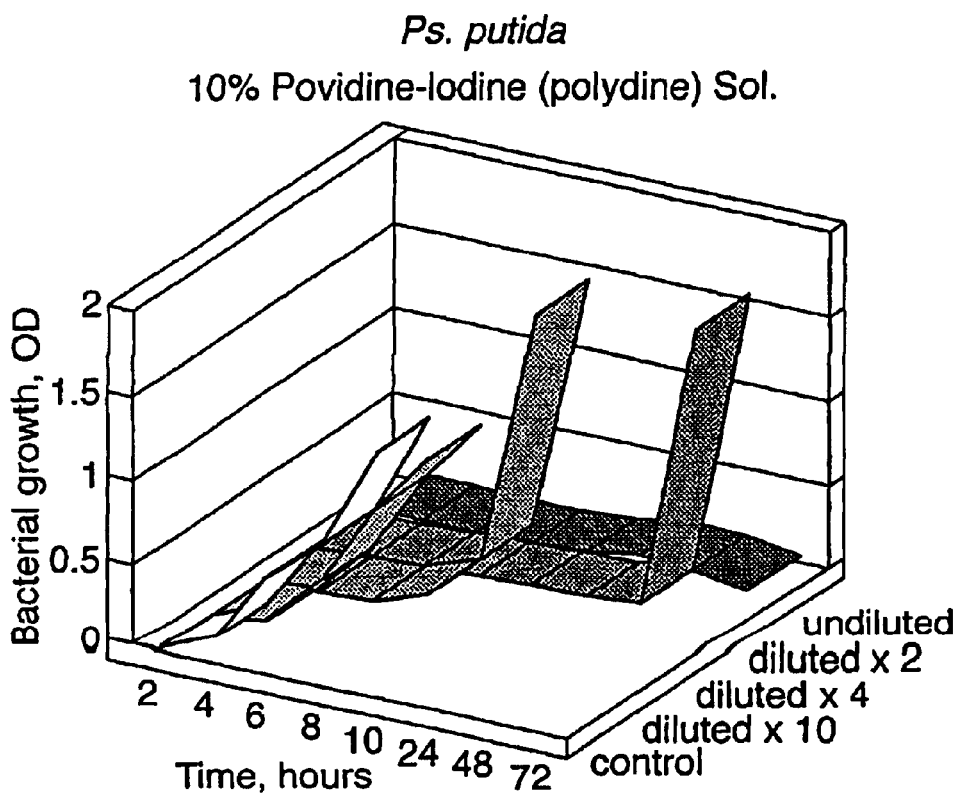

As presented in the figures, the MIC of the new formulations (FIGS. 7, 7a) were lower than the equivalent tincture (FIG. 8) and solution (FIG. 9). Unlike the non-TG-containing formulations, the new formulation totally eradicated the three microorganisms in its undiluted and X2 diluted forms. It should be noted that by the term undiluted, the investigators mean 4% solution in bacterial broth cultures. Povidone-iodine (PI) formulation with TG was also superior to a commercial formulation containing PEG 400 (FIGS. 10 and 11).

EXAMPLE 9

Figure 13:
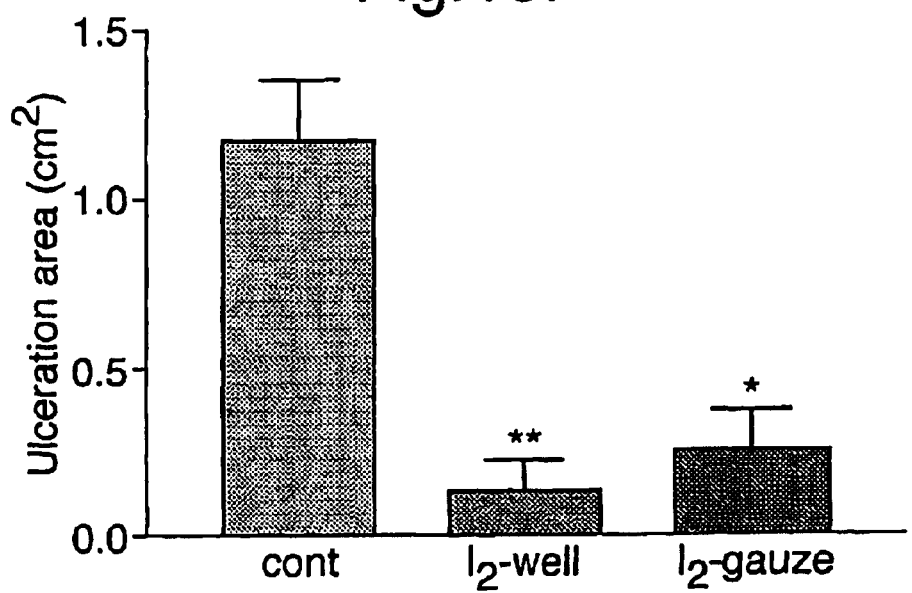
FIG. 13 is a graphic representation of the protective effect of iodine against thermal burns.

Protective Effect of Iodine Against Thermal Burns
Experimental Procedure: The procedure was carried out as described in FIG. 6 with the following exceptions: a) skin was exposed to 75° C. water for 7 sec; b) iodine was dissolved in TG only without addition of water; c) iodine was applied into a well (I$_2$ well, 3 animals) or as a gauze pad (I$_2$ gauze, 3 animals) soaked in iodine solution; d) lesions were evaluated 3 days after treatment.
Results: There was reduction of 89% and 79% in ulceration area after treatment with iodine by well and by iodine-soaked gauze, respectively (FIG. 13). **$p<0.01$, *$p<0.05$

EXAMPLE 10

Protective Effect of Iodine Against Skin Lesions Caused by SM

Figure 12:
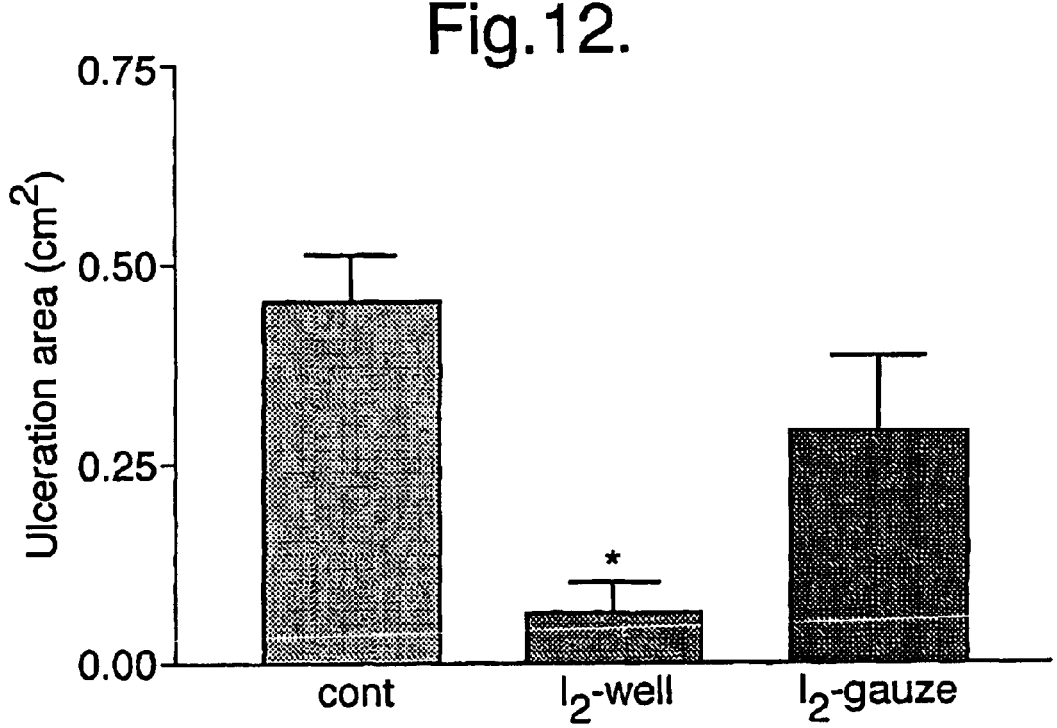
FIG. 12 is a graphic representation of the protective effect of iodine against skin lesions caused by SM.

The experimental procedure was similar to that described above with the exception that the stimulus was carried out by application of 1 μl SM and that iodine was applied 15 min after SM exposure. Results show reduction of 87% and 36% in ulceration area after treatment with iodine by well and by iodine-soaked gauze, respectively (FIG. 12). *$p<0.01$

EXAMPLE 11

Protective Effect of Iodine Against UV Irradiation

Guinea pigs were shaved and anesthetized as described in FIG. 1. Six wells were constructed on each back. The entire area of the animals, except the well area, was covered with foil. The animals were irradiated with UV-B (312 nm) at doses of 1.2 J/cm$^2$ and 2.4 J/cm$^2$. Three exposure sites of each animal were treated with 1 ml iodine (2% in TG) for 2 hours. Erythema was evaluated after 24 hours. Erythema score: 0-no irritation, 1-slight, 2-moderate, 3-marked irritation.

Results: There was marked reduction in skin erythema in iodine treated sites as compared to the sites without iodine treatment.

TABLE 2

Erythema score in guinea pigs after UV irradiation; protective effect of iodine.

|  | 1.2 J/cm$^2$ | 2.4 J/cm$^2$ |
|---|---|---|
| irradiated | 2 | 3 |
| irradiated and iodine treated | 0 | 0 |

EXAMPLE 12

Testing of Tween-80 as an Iodine Vehicle

Tween-80 is a detergent which dissolves molecular iodine. We have tested the following formulations of Tween-80, iodine, TG (tetraglycol) and water.

TABLE 3

Different Tween 80 formulations and their protective activity.

| Formulation | I$_2$ | TG | Tween-80 | water | % protection |
|---|---|---|---|---|---|
| 1 | 2% | 50% | 20% | 28% | 0% |
| 2 | 2% | 50% | 10% | 38% | 15% |
| 3 | 2% | 0 | 30% | 68% | 0% |
| 4 | 2% | 50% | 30% | 18% | 73% |
| 5 | 2% | 0 | 98% | 0 | 0% |

% protection means means percent of reducton in ulceration area in comparison to the control (SM exposure without treatment) group.

It is shown that iodine dissolved in Tween-80 was ineffective against SM-induced skin lesions (formulations 3 and 5). Addition of 50% TG to 30% Tween-80 was beneficial only in formulation 4 whereas omission of TG with the same Tween-80 concentration (formulation 3) nullified the protective effect iodine. These findings demonstrate the superiority of iodine-TG formulation and the inferiority of iodine-Tween-80 in their counter-irritating effect. The incorporation of Tween-80 in iodine-TG formulation caused reduction or prevention of its counter-irritating effect. Thus, in spite of being an iodine solvent, Tween-80 is not a suitable component in iodine formulation.

EXAMPLE 13

Figure 14:
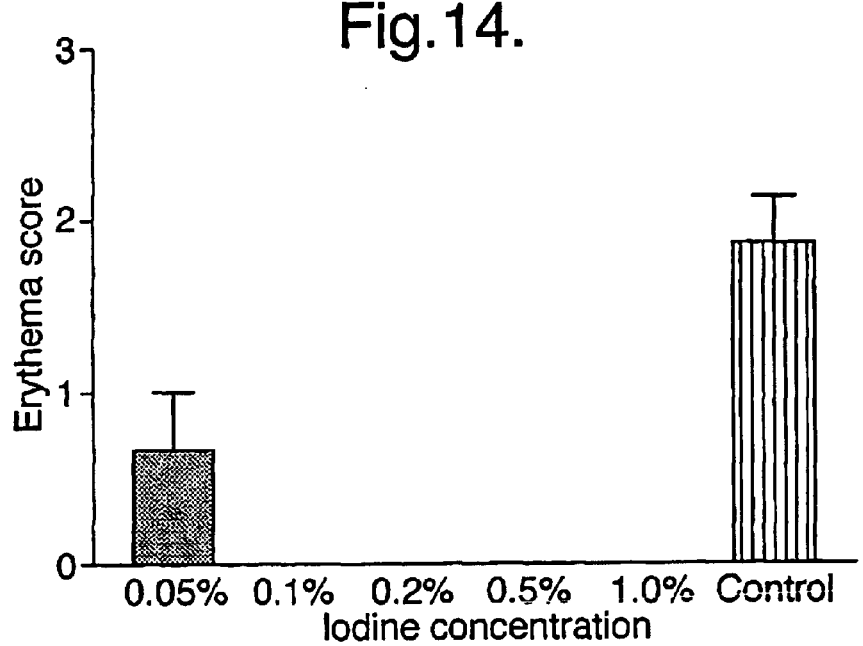
FIG. 14 is a graphic representation of the protective effect of different iodine concentrations against UV irradiation (5 min prophylaxis)

Different Iodin Formulations Used in Our Studies (from FIG. 14)

| Code | quantities (g) | | | | I$_2$ concentration (%) |
|---|---|---|---|---|---|
|  | I$_2$ | TG | PVP K-90 | DDW |  |
| IO-5 | 0.4 | 10 | 2 | 7.6 | 2 |
| IO-114 | 0.01 | 10 | 2 | 7.99 | 0.05 |
| IO-115 | 0.02 | 10 | 2 | 7.98 | 0.1 |
| IO-116 | 0.04 | 10 | 2 | 7.96 | 0.2 |
| IO-117 | 0.1 | 10 | 2 | 7.9 | 0.5 |
| IO-118 | 0.2 | 10 | 2 | 7.8 | 1 |
| IOP-77 |  | 25 | 5 | 20 | 0 |

Preparation of 20 g ointment: Solution A: Iodine was dissolved in 1 ml TG.
Solution B: A mixture of the entire amount of water and 9 ml TG was heated to 80° C. then PVP K-90 was slowly added into the heated solution until complete dissolution. Then Solution A was mixed well with solution B.

PVP K-90: polyvinylpyrrolidone (povidone) K-90; DDW: double distilled water Referring now to FIG. 14, there is shown the protective effect of different iodine concentrations against UV irradiation (5 min prophylaxis).

Area of 2×2 cm was exposed to Ultra Violet (UV) irradiation (312 nm, 3.6 J/cm$^2$). A thin layer of iodine ointment (40mg) was applied on the entire UV-exposed area 5 min prior irradiation. Erythema intensity was evaluated 5 days after exposure and scored from 0 to 4 while 0 means no effect and 4 means strong erythema.

It is shown (FIG. 14) that iodine concentrations at range of 0.1% to 1.0% no erythema was observed 5 days after exposure.

EXAMPLE 14

Figure 15:
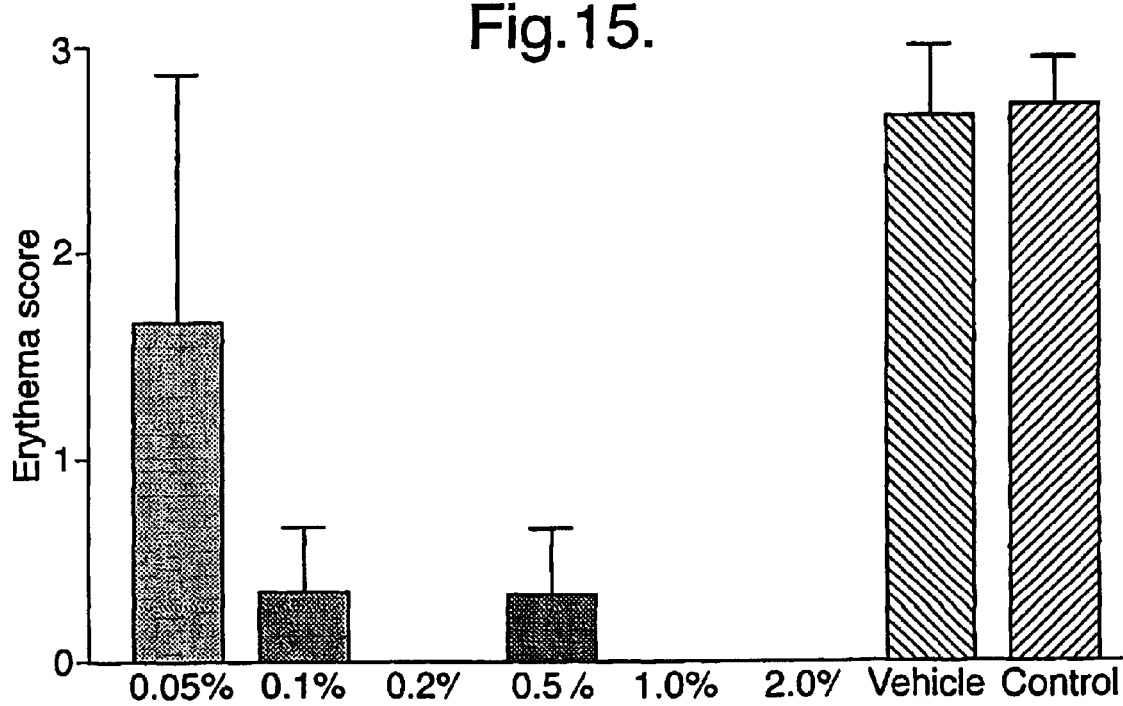
FIG. 15 is a graphic representation of the effect of different iodine concentrations against UV irradiation (10 min prophylaxis)

Referring to FIG. 15 there is seen the effect of different iodine concentrations against UV irradiation (10 min prophylaxis).

The experimental conditions were similar to that described in Example 13 with regard to FIG. 14, except for the fact that iodine was applied 10 min before irradiation and that the evaluation was carried out 3 days after treatment.

The reduction in the erythema is dearly demonstrated in 0.1% to 2% iodine whereas at the concentration of 0.05% the effect was much weaker. The vehicle (0% iodine) did not show protective effect.

EXAMPLE 15

Figure 16:
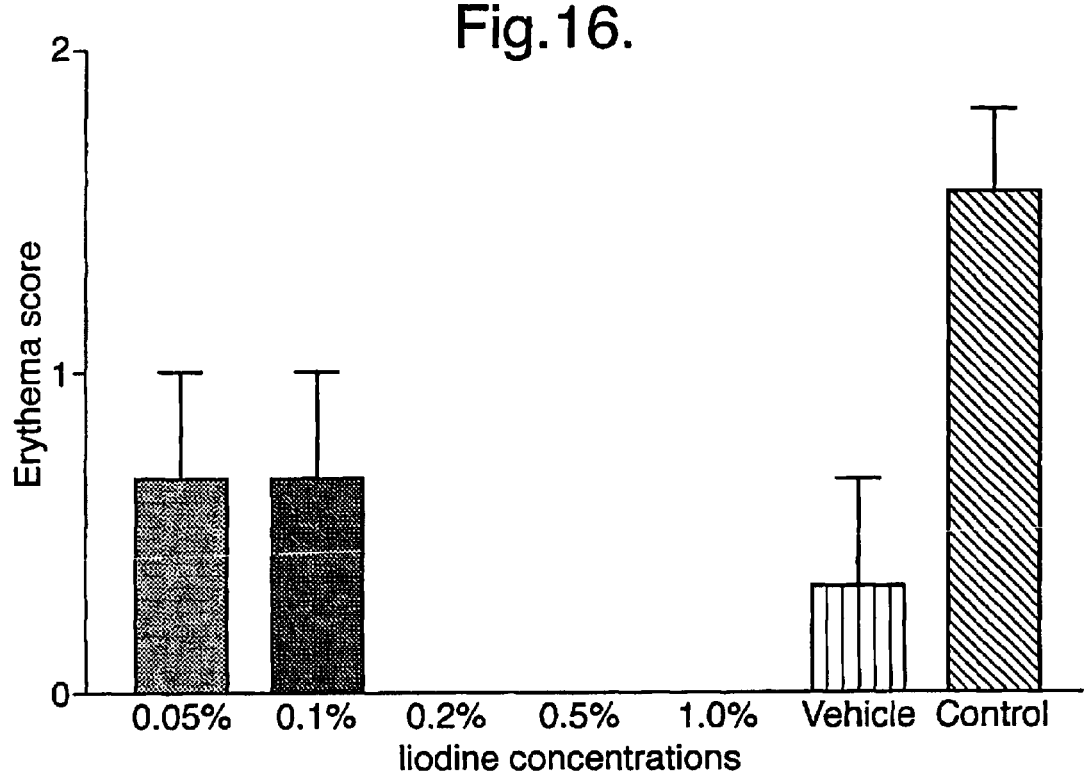

Referring to FIG. 16 there is seen the effect of different iodine concentrations against UV irradiation (30 min prophylaxis).

The experimental conditions were similar to that described in Example 13 with regard to FIG. 14, except for the fact that iodine was applied 30 min before irradiation and that the evaluation was carried out 4 days after treatment.

The reduction in the erythema is clearly demonstrated in 0.2% to 1% iodine whereas at the concentration of 0.05% and 0.01% the effect was much weaker. In this case the vehicle (0% iodine) showed significant protective effect.

EXAMPLE 16

Figure 17:
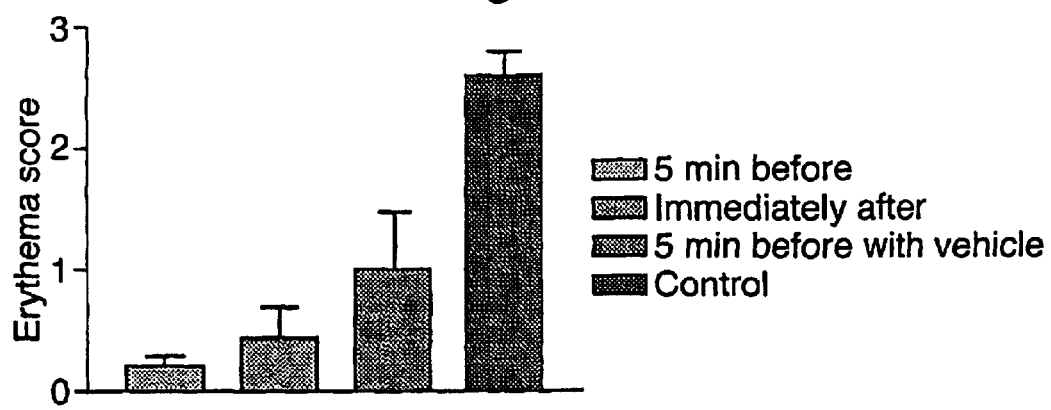
FIG. 17 is a graphic representation of the effect of iodine against UV irradiation.

Referring to FIG. 17 there is seen the effect of iodine against UV irradiation. The experimental conditions were similar to that described in Example 13 with regard to FIG. 14, except for the fact that 2% iodine (IO-5 formulation) and its vehicle (IOP-77) were tested. Iodine was applied 5 min before and immediately after irradiation and the vehicle was applied 5 min before irradiation. The evaluation was carried out 3 days after treatment.

The reduction in the erythema is clearly demonstrated in 2% iodine treatment. The maximal effect was obtained with prophylactic treatment and also, but to a lesser extent, with immediate post-exposure treatment. The vehicle showed also a protective effect by prophylactic treatment but much weaker than that observed with iodine.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A composition of matter comprising molecular iodine, tetraglycol and an aqueous diluent.

2. A composition of matter according to claim 1, wherein said iodine is present in said composition in a concentration of between about 0.00001 and 50% by weight.

3. A composition of matter according to claim 1, wherein said tetraglycol is present in said composition at a concentration of between 1 and 99% by weight.

4. A composition according to claim 1, wherein said molecular iodine is released from an iodine-containing and/or producing agent selected from the group consisting of cadexomer-iodine, diiodhydrin, domiodol, hydriodic acid; iodinated glycerol, iodoform, and povidone-iodine.

5. A method for treating a wound comprising administering an effective amount of the composition of claim 1.

6. A method for treating a wound according to claim 5, wherein the wound is a skin burn.

7. A method for treating a wound according to claim 5, wherein the wound is a chemical burn.

8. A method for treating a wound according to claim 5, wherein the wound is a thermal burn.

9. A pharmaceutical composition comprising molecular iodine, tetraglycol, and an aqueous diluent.

10. A pharmaceutical composition according to claim 9, wherein said molecular iodine is released from an iodine-containing and/or producing agent selected from the group consisting of cadexomer-iodine, diiodhydrin, domiodol, hydriodic acid, iodinated glycerol, iodoform, and povidone-iodine.

11. A method of preparing a topical antiseptic agent comprising adding tetraglycol as a solvent to molecular iodine and diluting the resulting mixture with an aqueous diluent.

12. A method of preparing a topical counter-irritant for skin burns comprising adding tetraglycol as a solvent to molecular iodine and diluting the resulting mixture with an aqueous diluent.

13. A method of preparing a topical counter-irritant for chemical and thermal bums comprising adding tetraglycol as a solvent to molecular iodine and diluting the resulting mixture with an aqueous diluent.

* * * * *